United States Patent [19]
Wickham

[11] 3,983,881
[45] Oct. 5, 1976

[54] MUSCLE STIMULATOR

[75] Inventor: Geoffrey Gordon Wickham, Longueville, Australia

[73] Assignee: Telectronics Pty. Limited, Australia

[22] Filed: May 21, 1975

[21] Appl. No.: 579,506

[52] U.S. Cl. .............................. 128/421; 128/422
[51] Int. Cl.² ........................................ A61N 1/36
[58] Field of Search ............ 128/2.1 R, 419 R, 420, 128/421, 422, 423

[56] References Cited
UNITED STATES PATENTS

| | | | |
|---|---|---|---|
| 2,099,511 | 11/1937 | Caesar | 128/423 |
| 2,700,975 | 2/1955 | Hopfinger et al. | 128/421 |
| 3,773,051 | 11/1973 | Holcomb et al. | 128/422 |
| 3,810,457 | 5/1974 | Bottcher et al. | 128/421 |

FOREIGN PATENTS OR APPLICATIONS

| | | | |
|---|---|---|---|
| 974,944 | 6/1961 | Germany | 128/422 |

*Primary Examiner*—William E. Kamm
*Attorney, Agent, or Firm*—Flehr, Hohbach, Test, Albritton & Herbert

[57] ABSTRACT

An improved muscle stimulator, particularly suited to long term rhythmic stimulation for the selective development of musculature otherwise asymmetric or retarded in relative development. To minimize the subjects' awareness of stimulation, to permit nocturnal use, and to minimize battery consumption, the energy content of each pulse train is modulated by a progressive increase of pulse width up to a maximum, followed by a progressive decrease of pulse width, thus yielding a gradual contraction and relaxation of the muscle.

5 Claims, 9 Drawing Figures

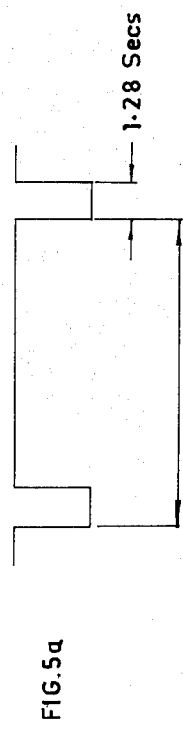
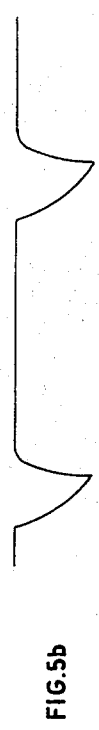
FIG.5a
FIG.5b
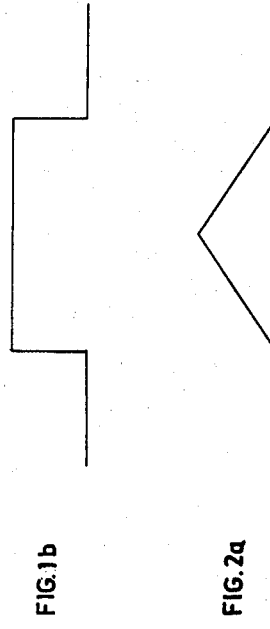
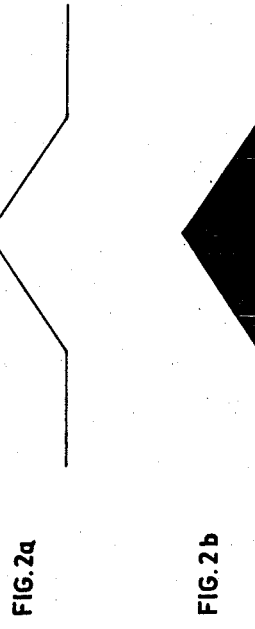
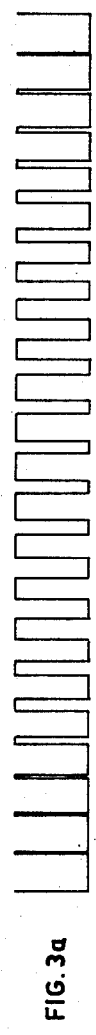
FIG.1a
FIG.1b
FIG.2a
FIG.2b
FIG.3a
FIG.3b

MUSCLE STIMULATOR

BACKGROUND OF THE INVENTION

The response of muscle to an electrical current is believed to have been first observed and recorded by Galvani in 1791. All muscle is comprised of excitable cells which may be stimulated to contract by an applied electrical or chemical stimulus. The present invention is concerned only with skeletal and visceral muscle (sometimes referred to as striated and smooth muscle respectively) and not cardiac muscle in which the cells have a natural capacity for rhythmic contraction and a mutual coupling mechanism between cells. By contrast, skeletal and visceral muscle cells depolarize and contract only when acted upon by specific stimuli. Moreover, in skeletal and visceral muscle a depolarization does not naturally spread from a first depolarized cell to surrounding cells as in the case of cardiac muscle and this characteristic poses particular problems in artificially stimulating skeletal and visceral muscle. Cell depolarization in response to a natural stimulus is initiated at a multitude of sites within the muscle called synaptic clefts into which a chemical transmitter is released by specialized nerve bundles, the synaptic knobs.

Artificial electrical stimulation of muscle contraction by electrodes placed upon or into the muscle is thus a complex response of both muscle cells and nerve cells to the artificial stimulus. In order that either muscle cells or nerve cells may be depolarized, a given amount of work (the product of electrical current times time) must be done. At minimum current levels only those cells immediately interfacing the electrode will be depolarized and as the current is increased those cells further away will also be depolarized. Where nerve cells are incorporated within the area of muscle subjected to current flow, above a threshold value, then muscle cells beyond the perimeter of the above threshold current flow can be depolarized by nerve propagation.

Thus, in general, it can be suggested that the magnitude of muscle contraction (that is the percentage of the cell total that is depolarized) is a function of stimulus intensity. In practice, in order to distribute the artificial contraction in an even manner the stimulus must be distributed by placing a multiplicity of electrodes on or into the muscle.

Further, it is known that the ability of a cell to respond to a stimulus of given current magnitude is related to the duration of time during which the current flows. This is often expressed graphically as a "Strength-Duration Curve". Within limits, a reduction in time may be compensated by an increase in current. The forgoing data is well known to those experienced in the art. In man, artificial electrical stimulation of visceral and skeletal muscle has been employed therapeutically with limited success since the early 1960's.

In attempted control of the neurogenic bladder, stimulation of the detrusor, external sphincter and the bladder wall has been tried. The electrical parameters employed varied greatly as may be anticipated. Pulse voltages of 2 to 45 volts, pulse durations of 0.5 to 5 mSec, and pulse repetition frequencies of 10 to 25 Hz are recorded. In this application a burst or train of pulses within the range of parameters nominated is manually started and stopped. In an article entitled "Radio Frequency Electrophrenic Stimulation" by John P. Judson, M.D., and William L. Glenn, M.D., Journal American Medical Association, 203.12 (1968), pp. 1033–1037, there is reported artificial stimulation of respiration by stimulating the phrenic nerve with pulses of 0.1 mSec duration at 60 Hz repetition frequency and in trains of 1.7 Secs duration. Another article, entitled "Electrical Stimulation of Excitable Tissue by Radio-Frequency Transmission" by William W. L. Glenn, M.D., et al, Annals of Surgery, Sept. 1964, pp. 338–350 relates generally to the subject of electrical stimulation and at page 339 describes what is probably the first therapeutically applied modulated pulse train intended to give a smooth control of inspiration and exhalation. This is gained by amplitude modulating the pulses of the wave train; the pulse width, repetition frequency and train duration remaining constant.

SUMMARY OF THE INVENTION

This invention relates to electrical stimulation of muscle and particularly to electrical stimulation applied to muscle, long term, to produce a rhythmic contraction and relaxation of the muscle. Such stimulation constitutes artificial exercise of the muscle and may be selectively applied to one muscle (or a related muscle group) such as to develop or strengthen that muscle only, unlike natural exercise with which only limited selectivity is possible.

More specifically, the invention is incorporated in a muscle stimulator wherein a pulse width modulated train of electrical pulses is applied to muscle. The width of the pulse may be modulated by a progressive or exponential increase in pulse width, followed by a progressive or exponential decrease in pulse width.

BRIEF DESCRIPTION OF THE DRAWING

FIG. 1a is a wave diagram showing a pulse train which produces relatively unsatisfactory muscle response;

FIG. 1b is a diagram showing muscle response from the pulse train shown in FIG. 1a;

FIG. 2a is a diagram showing an ideal form of muscle response;

FIG. 2b is a wave diagram showing a pulse train suitable to produce the muscle response shown in FIG. 2a;

FIG. 3a is a wave diagram showing a pulse train in accordance with the present invention;

FIG. 3b is a diagram showing muscle response from the pulse train shown in FIG. 3a;

FIG. 5a is a diagram showing the output of NAND gate 29 of FIG. 4; and

FIG. 5b is a diagram showing the bias applied to transistor 35 of FIG. 4.

DESCRIPTION OF THE PREFERRED EMBODIMENT

Figure 4:
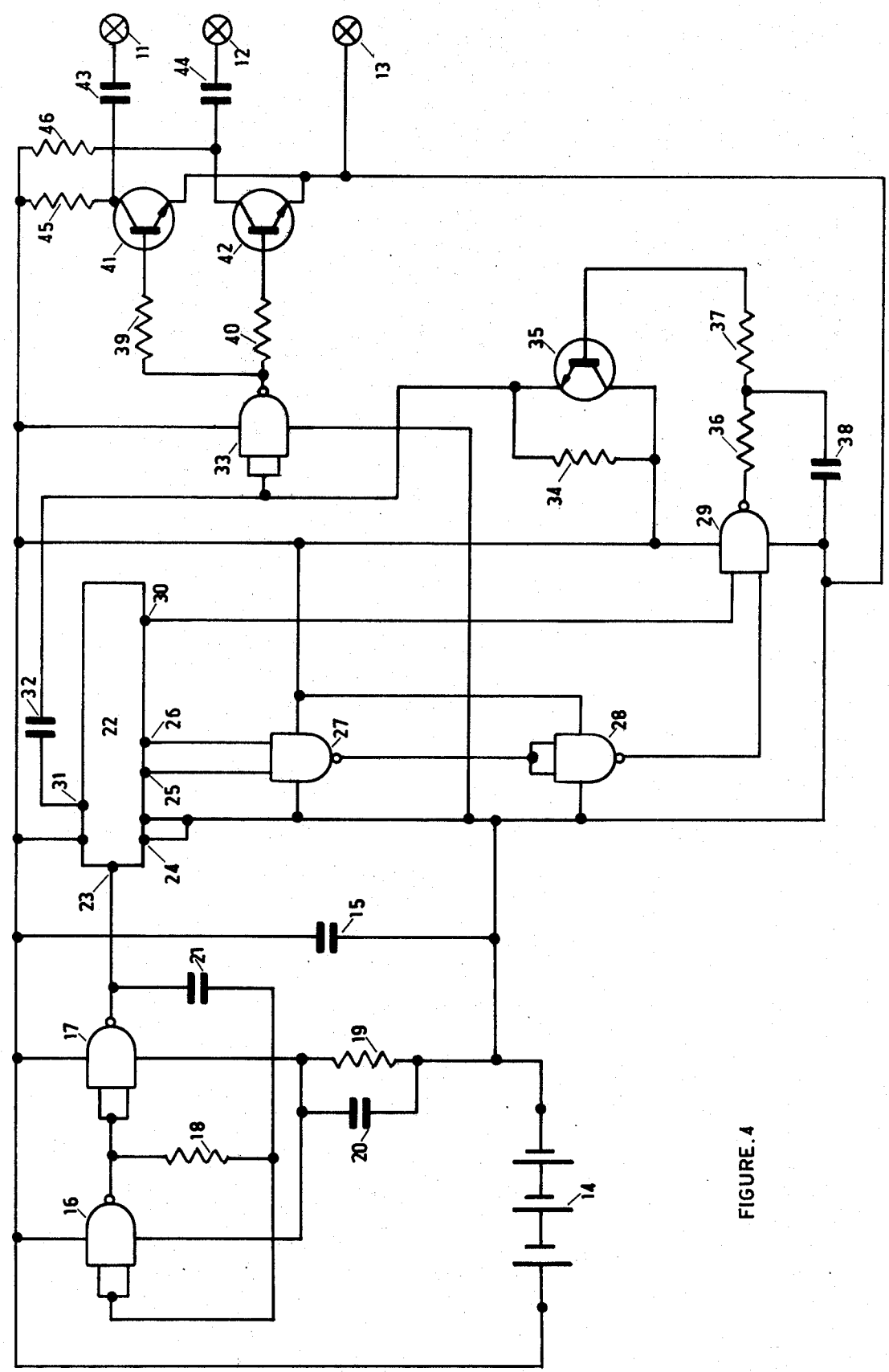
FIG. 4 is a schematic circuit diagram of a muscle stimulator in accordance with the invention.

The work which specifically led to the concept claimed herein, involved rhythmic stimulation of muscle contraction.

In childhood, approaching adolescence, a proportion of the populace evidences a slight curvature of the lower spine. In the presence of certain other diagnostic indicators, it can be prognosed that this scoliotic curvature will progress to a severe deformity and chronic disability. Although the etiopathogenesis of the disease is not clearly understood, and may be significantly different in different subjects, it appears that satisfactory control and, potentially, reversal of the deformity may be gained by artificially exercising and hence strengthening a muscle group on the concave side of the spinal curvature.

The parameters of voltage, current, pulse width, pulse repetition frequency and pulse train duration employed to this purpose are within the order of such parameters in the work of others. Empirically, a pulse voltage of 3.4 volts, a pulse duration maximum of 1.5 mSec., a pulse repetition frequency of 50 Hz, a pulse train duration of approximately 1½ seconds and a pulse train repetition interval of approximately 10 seconds have been chosen.

The stimulator has been designed as a completely implantable device (in the manner of a heart pacer) to ease the physicians' problems of patient management. This is particularly important with children and moreover, allows the stimulator to be operated at night without the restraint on nocturnal rolling which would be necessary with a device applied externally to the patient. To be satisfactorily implantable for children the stimulator must be small, thus imposing a considerable constraint upon the amount of battery energy that may be incorporated. Additionally, the stimulator once implanted should perform its function for at least two years before it becomes necessary to reoperate because of exhausted batteries. The simplest manner in which the muscle could be stimulated is by rhythmic pulse trains as illustrated in FIG. 1a and this form of pulse train has the advantage that it may be generated economically with a minimum of battery energy waste. It minimizes battery waste because it can be produced by on/off switching functions alone, and energy is only wasted during the short transitions from on to off. However, this form of pulse train evokes a muscle response as shown by FIG. 1b; a sharp contraction which is held and then terminated by a sharp relaxation. This type of muscle response would be of considerable discomfort to the patient and would inhibit satisfactory sleep patterns. An ideal form of muscle response is that shown by FIG. 2a, a gradual increase in the magnitude of the contraction, up to a maximum, followed by a gradual relaxation phase. This manner of muscle response can be produced by a stimulating wave train as illustrated by FIG. 2b, in which the amplitude of the pulses is modulated. However, this form of control of pulse energy involves a major waste of battery energy; approximately the same amount of energy is dissipated in the pulse generator as is transmitted to the muscle.

The present invention is directed to attaining the more ideal manner of muscle response without the waste of battery energy. It is accomplished by varying the width of the pulses in each pulse train. Theoretically, considering the strength-duration equation for cellular stimulation previously referred to, for any given pulse voltage and current, a finite minimum pulse width exists at which depolarization of cells at the electrode interface will occur.

As the pulse width is increased cells farther distant are depolarized and thus the magnitude of the muscle contraction may be controlled. A stimulator producing pulse trains, as shown by FIG. 3a, was tested and shown to produce a muscle response similar to FIG. 3b.

As this manner of wavetrain can be generated using on/off switching elements, the electrical efficiency is high, greater than 90%. The generation and application of this manner of wave train for controlled muscle contraction is the essence of the present invention.

Although the invention is described with reference to one specific embodiment and for one particular therapeutic application it should be recognized that wide variations in the form of the stimulator, including those dictated by alternative therapeutic applications, may be made while continuing to employ the essence of the invention and be within its spirit and scope.

The operation of the illustrative embodiment of the invention is described with reference to FIG. 4.

Terminals 11, 12, and 13 are provided for connection to electrodes (not shown) coupling the stimulating pulses to the muscle. In this embodiment there are employed two cathodically pulsed electrodes, for connection to terminals 11 and 12 and one anodic electrode for connection to terminal 13. However, a greater or lesser number of electrodes may be used depending upon the specific clinical application.

A battery 14, includes therein mercury cells in series to give a supply potential of 4.08 volts. A capacitor 15 bypasses the battery supply to ensure a low impedance source. NAND gates 16 and 17 with associated resistors 18 and 19 and capacitors 20 and 21 form a free running pulse generator, or logic clock, operating at a frequency of 100 Hz. Assuming that the output of gate 17 has switched from logic level 0 to logic level 1, the inputs to gate 16, wired as an inverter, will be switched, by way of capacitor 21, to logic level 1. The output of gate 16 and the inputs to gate 17, also wired as an inverter, will be at logic level 0, thus sustaining the logic level 1 status at the output of gate 17. The charge on capacitor 21 will leak away through resistor 18 until the potential at the inputs to gate 16 falls from logic level 1 to the logic level 0 input region of gate 16. The output of gate 16 thus immediately switches to logic level 1, switching the output of gate 17 to logic level 0, reversing the charge on capacitor 21 and a new half cycle commences.

Thus the frequency of oscillation is essentially determined by the time constant of resistor 18 and capacitor 21 and in the embodiment described herein is approximately 5mSecs per half cycle of the clock. The function of the resistor 19, connected from the negative battery supply to gates 16 and 17 and bypassed by capacitor 20, is to minimize the current drawn by the clock during that part of each half cycle when the voltage at the inputs of gate 16 is passing through the linear operating region of that gate.

The output of the clock is connected to a binary counter or divider 22. The binary counter 22 is a twelve bit counter, but in the present embodiment only ten bits are utilized. The output from gate 17 of the clock is coupled to a clocking input 23 of counter 22. A reset terminal 24 is held permanently at logic level 0 so that the binary counter advances one bit at each transition of the clock from logic level 1 to logic level 0. Binary outputs 25 and 26 (counts of 256 and 512 respectively) are coupled to the inputs of NAND gate 27.

Output 25 changes state from logic level 1 to logic level 0 every 2.56 seconds (count of 256) and output 26 changes state from logic level 1 to logic level 0 every 5.12 seconds (count 512). Coincidence of logic levels 1 at the inputs of NAND gate 27 produces a logic level 0 output. The output of gate 27, normally at logic level 1, thus goes to logic level 0 for 1.28 seconds each 5.12 seconds. NAND gate 28 inverts the output of gate 27, and this inverted output is applied to the lower input of NAND gate 29.

The upper input of NAND gate 29 is derived from binary output 30 (count of 1024) of counter 22. This output undergoes a logic level 1 to 0 change of state each 10.24 seconds.

The output 31 (count of 2) of binary counter 22, undergoes one complete cycle each 20 mSecs. This is coupled by way of capacitor 32 to inverter wired inputs of NAND gate 33. The inputs of gate 33 are biased to logic level 1 by resistor 34, which with capacitor 32 forms a critical time constant. The leading edge of each logic level 0 half cycle at terminal 31 drives the inputs of gate 33 to logic level 0, and commences a logic level 1 pulse at the output of gate 33. The time constant of capacitor 32 and resistor 34 (ignoring transistor 35) determines the time period during which the 10 mSec logic level 0 pulse at terminal 31 holds the output of gate 33 at logic level 1. The transistor 35, is in parallel with the time constant resistor 34, for a negative polarity at the inputs to gate 33. As previously stated, the output of NAND gate 29 is normally at logic level 1. Thus, by way of resistors 36 and 37 the transistor 35 is normally forward biased. With transistor 35 forward biased the output pulse width of gate 33 is very short, typically less than 1% of the time constant of capacitor 32 and resistor 34.

As earlier stated, and as shown in FIG. 5a, the output of NAND gate 29 goes from logic level 1 to 0 for 1.28 seconds each 10.24 seconds. As shown in FIG. 5b, the time constant of resistor 36 and capacitor 38 is set such that during the 1.28 second logic level 0 pulse from gate 29, the initially forward bias at the base of transistor 35 decreases exponentially until the transistor 35 presents negligible current flow in shunt with resistor 34 at the end of the 1.28 second period. The bias on the transistor 35 is then exponentially re-established.

Thus, each 10.24 seconds, the normally very short (approximately 5μSec) pulses appearing at the output of gate 33 at 20mSec intervals will commence to increase in pulse width in an approximately exponential manner until a maximum width of approximately 1.5 mSec is reached, the successive pulse widths then decrease in an approximately exponential manner until the original condition is re-established. This sequence is illustrated (not to scale) by FIG. 3a. FIG. 3b illustrates the consequent exponentially rising and falling energy distribution of the sequence.

A small improvement in the operation of this circuit may be made by incorporating a resistance in series with the capacitor 32 such that the current sinking provided by transistor 35, in its maximum forward biased condition, will reduce the pulse voltage at the inputs of gate 33 to a level lower than the logic transition level. Thus, during the period when transistor 35 is in its maximum forward biased condition there will be no output pulses at the output of gate 33, rather than the continual sequence of very short pulses. The logic level 1 pulses at the output of gate 33 are coupled by way of resistors 39 and 40 to the two common emitter output stages, transistors 41 and 42, so that each logic level 1 pulse at gate 33 forward biases both transistors 41 and 42. Each time transistors 41 and 42 are forward biased, some charge is transferred from the capacitors 43 and 44 to the terminals 11 and 12 and by way of the electrodes (not shown) to the common terminal 13. During the period between output pulses, the charge upon capacitors 43 and 44 is restored by the resistors 45 and 46.

Alternative to employing separate output stages for each electrode, and with some consequent asymmetry of cathodic pulse current, a single output transistor may be employed with a single output coupling capacitor, and all the cathodic electrodes operated electrically in parallel. In such an arrangement a lower value for the collector resistance and a higher value of output coupling capacitance must be employed.

The aforementioned circuit has been successfully constructed using the specific components listed below in Table I.

TABLE I

| Battery | |
|---|---|
| 14 | 3 RM1cc mercury cells |
| Counter | |
| 22 | Twelve bit binary counter MC14040cp. C.Mos. Manufactured by Motorola Semiconductor Products, Inc. |
| Gates | |
| 16,17,27, 29,33 | Each is one-fourth of a Mc14011AL quad NAND gate. C.Mos. Manufactured by Motorola Semiconductor Products, Inc. |
| Transistors | |
| 35,41,42 | BC109 |
| Capacitors | |
| 14,43,44 | 33μfd |
| 20,21,32 | 2200 μμf |
| 38 | 0.47μfd |
| Resistors | |
| 18,36 | 2.2 M ohm |
| 19 | 220 K ohm |
| 34 | 1 M ohm |
| 37 | 120 K ohm |
| 39,40 | 22 K ohm |
| 45,46 | 1.8 K ohm |

What is claimed is:

1. A muscle stimulator for stimulating muscles having excitable cells comprising circuit means for generating a train of constant amplitude electrical pulses, terminal means connected to said circuit means adapted to electrically couple the circuit means to electrodes located at the muscle to be stimulated, said circuit means including modulation means for progressively and continuously increasing the width of the electrical pulses in said train from a minimum magnitude at which only those cells at the interface with the electrode are depolarized to a maximum magnitude at which cells remote from the electrode interface are depolarized and then progressively and continuously decreasing the pulse width to the minimum magnitude.

2. A muscle stimulator as defined in claim 1 wherein said means for modulating the width of the electrical pulses comprises means for exponentially increasing the width of said pulse to a maximum and for exponentially decreasing the width of said pulses from said maximum to a minimum.

3. A muscle stimulator as defined in claim 1 wherein said circuit means includes means for applying said electrical pulses to said terminal means at a constant pulse repetition frequency.

4. A muscle stimulator as defined in claim 1 wherein said circuit means includes means for developing a pulse train having a pulse repetition frequency of approximately fifty pulses per second, a pulse train duration of about one and one-half seconds and a pulse train repetition interval of about ten seconds.

5. A muscle stimulator as defined in claim 4 wherein said means for modulating the width of said electrical pulses includes means for limiting the width of said pulses to about 1½ milliseconds.

* * * * *